(12) United States Patent
Ikehara et al.

(10) Patent No.: US 8,388,950 B2
(45) Date of Patent: Mar. 5, 2013

(54) COENZYME $Q_{10}$-CONTAINING WATER-SOLUBLE COMPOSITION AND PROCESS FOR PRODUCTION THEREOF

(75) Inventors: Toshinori Ikehara, Takasago (JP); Hideyuki Kishida, Kakogawa (JP)

(73) Assignee: Kaneka Corporation, Osaka (JP)

( * ) Notice: Subject to any disclaimer, the term of this patent is extended or adjusted under 35 U.S.C. 154(b) by 746 days.

(21) Appl. No.: 11/917,454

(22) PCT Filed: Jun. 14, 2006

(86) PCT No.: PCT/JP2006/311933
§ 371 (c)(1),
(2), (4) Date: Jul. 19, 2010

(87) PCT Pub. No.: WO2006/134970
PCT Pub. Date: Dec. 21, 2006

(65) Prior Publication Data
US 2010/0284983 A1 Nov. 11, 2010

(30) Foreign Application Priority Data

Jun. 15, 2005 (JP) ................................. 2005-174917

(51) Int. Cl.
*A61K 38/43* (2006.01)
(52) U.S. Cl. ...................................................... 424/94.1
(58) Field of Classification Search .................... None
See application file for complete search history.

(56) References Cited

U.S. PATENT DOCUMENTS

| 5,565,557 | A * | 10/1996 | Koyama et al. | ......... 536/123.13 |
| 6,048,566 | A | 4/2000 | Behnam et al. | |
| 8,067,217 | B2 * | 11/2011 | Ueda et al. | .................... 435/188 |
| 2005/0147598 | A1 * | 7/2005 | Ueda et al. | .................... 424/94.1 |
| 2005/0226858 | A1 * | 10/2005 | Kitamura et al. | ............ 424/94.1 |
| 2006/0073176 | A1 | 4/2006 | Segawa et al. | |
| 2006/0134085 | A1 | 6/2006 | Yamaguchi et al. | |
| 2006/0147542 | A1 * | 7/2006 | Ono et al. | ..................... 424/490 |

FOREIGN PATENT DOCUMENTS

| JP | 58-013508 A | 1/1983 |
| JP | 2000-212066 A | 8/2000 |
| JP | 2001-504343 A1 | 4/2001 |
| JP | 2003-238396 A | 8/2003 |
| JP | 2003-284510 A | 10/2003 |
| JP | 2003-300870 A | 10/2003 |
| JP | 2003-304847 A | 10/2003 |
| JP | 2003-313772 A | 11/2003 |
| JP | 2004-26734 A | 1/2004 |
| JP | 2004-026734 A | 1/2004 |
| JP | 2004-196781 A | 7/2004 |
| JP | 2004-210669 A | 7/2004 |
| JP | 2004-242509 A | 9/2004 |
| JP | 2005-97161 A | 4/2005 |
| JP | 2005-097161 A | 4/2005 |
| JP | 2005-325086 A | 11/2005 |
| JP | 2006-22064 A | 1/2006 |
| JP | 2006-022064 A | 1/2006 |
| WO | 2004/064543 A1 | 8/2004 |

* cited by examiner

*Primary Examiner* — Karen Cochrane Carlson
*Assistant Examiner* — Natalie Moss
(74) *Attorney, Agent, or Firm* — Sughrue Mion, PLLC

(57) ABSTRACT

A coenzyme $Q_{10}$-containing water soluble composition comprises coenzyme $Q_{10}$, a hydrophilic polyglycerol fatty acid ester, a lipophilic sucrose fatty acid ester and an aqueous phase component and a process for producing the same are disclosed. A coenzyme $Q_{10}$-containing water-soluble dry powder can be obtained by drying the above-mentioned coenzyme $Q_{10}$-containing water soluble composition. A food, functional food, beverage, pharmaceutical product, quasi drug, cosmetic, or animal food can be obtained by using the above-mentioned coenzyme $Q_{10}$-containing water soluble composition or the above-mentioned coenzyme $Q_{10}$-containing water-soluble dry powder. The coenzyme $Q_{10}$-containing water soluble composition has a high bioavailability, and maintains a stable emulsion form for a long period of time from refrigeration temperature to room temperature and allows efficient supply.

12 Claims, 1 Drawing Sheet

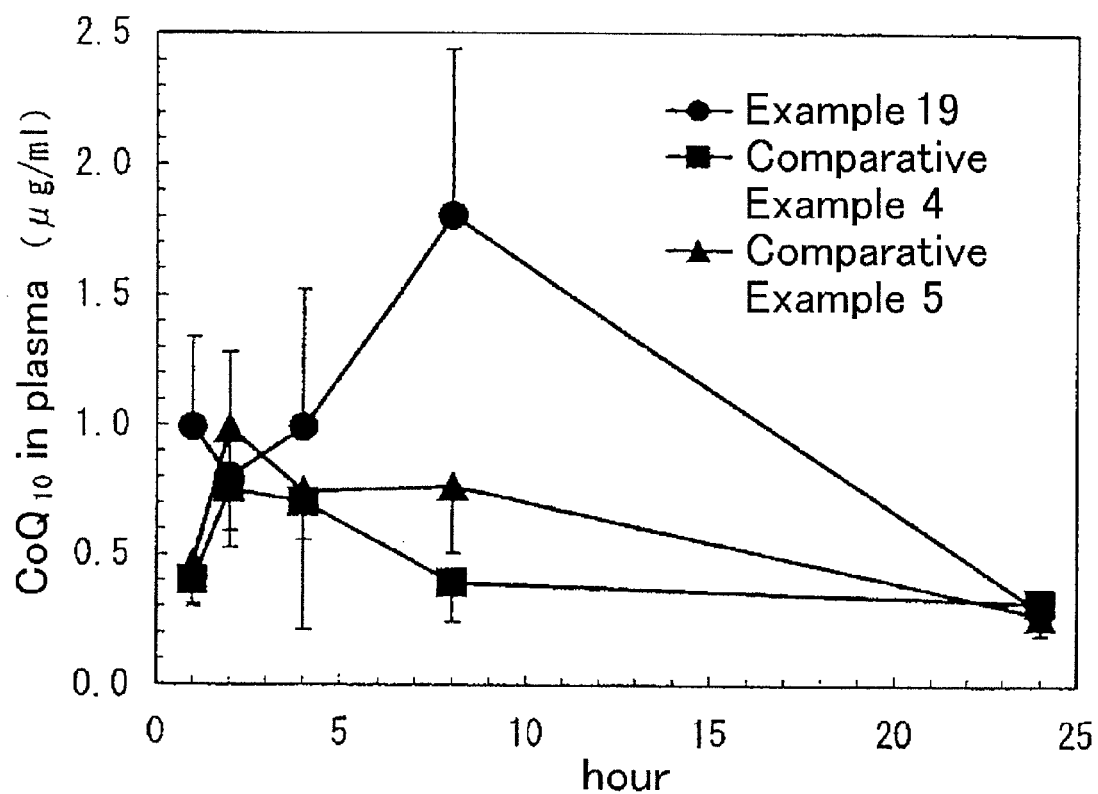

COENZYME $Q_{10}$-CONTAINING WATER-SOLUBLE COMPOSITION AND PROCESS FOR PRODUCTION THEREOF

TECHNICAL FIELD

The present invention relates to a coenzyme $Q_{10}$-containing water soluble composition and a process for producing the same, and more particularly, to a coenzyme $Q_{10}$-containing water soluble composition with high bioavailability.

BACKGROUND ART

Coenzyme $Q_{10}$ is a benzoquinone derivative and known to be localized in the mitochondrion, lysosome, Golgi body, microsome, peroxisome, and cell membrane, among others, and involved, as constituents of the electron transport system, in ATP production and activation, in vivo antioxidant activity, and membrane stabilization; it is thus a substance indispensable for body function maintenance. Coenzyme $Q_{10}$ is not only supplied from diets but also biosynthesized in the body, but it is known that the content thereof in the body is markedly decreased due to aging and various stresses to which the living body is subjected. In addition, the tissue coenzyme $Q_{10}$ concentration is estimated to be decreased under conditions where peroxides are easily produced in the living body, such as hard exercises or overfatigue. Decrease in the coenzyme $Q_{10}$ content in the body characteristically lead to decreased productivity of ATP, decreased cardiac function, decreased resistance to oxidation stress, and instability of biomembranes, thus being deleterious to health. Therefore, to make up for a shortage of coenzyme $Q_{10}$ is advantageous for promoting energy production in mitochondria, enhancing the antioxidant capacity of the living body, and maintenance of homeostasis.

As for supplying coenzyme $Q_{10}$, which is indispensable for maintaining biological functions but tends to be decreased and insufficient due to aging and stress as mentioned above, coenzyme $Q_{10}$ has already been supplied exclusively as a drug or as a food supplement in the form of tablets or capsules. It is well known, however, that oral absorption of coenzyme $Q_{10}$ is poor since the solubility thereof in water is very low. Thus, since coenzyme $Q_{10}$ has very low solubility in water and alcohol, and also solubility in oils is low, emulsification thereof by an oil-in-water method is generally difficult. Furthermore, even if an oil-in-water emulsion can be temporarily obtained, there arises a problem that crystallization of coenzyme $Q_{10}$ occurs in a short period which leads to emulsion breaking or solidification.

Patent Document 1 discloses a technology of using polyoxyethylene sorbitan monooleate for producing a beverage containing coenzyme $Q_{10}$. The use of such an ethylene oxide-based surfactant has a risk for causing hemolysis, mucosal irritation, mucosal defect and the like and, in many cases, utilization thereof in food applications is actually hesitated.

Patent Document 2 discloses a technology of processing coenzyme $Q_{10}$ with a high pressure using an emulsifier and polyhydric alcohol as aqueous solutions for dissolving liposoluble substances. Since the effect of preventing coenzyme $Q_{10}$ crystallization is not sufficient, crystallization occurs and proceeds with time and therefore the oil-in-water emulsion cannot be maintained.

Patent Document 3 discloses a technology of using a medium chain fatty acid ester for preventing coenzyme $Q_{10}$ crystallization and obtaining a stable oil-in-water emulsion. This technology requires use of a large amount of medium chain fatty acid ester for dissolving coenzyme $Q_{10}$ and it is, however, difficult to obtain a product containing coenzyme $Q_{10}$ at high ratio.

Patent Document 4 discloses a water-soluble composition containing coenzyme $Q_{10}$ and oil. Since the effect of preventing coenzyme $Q_{10}$ crystallization is not sufficient, crystallization occurs and proceeds with time and therefore the oil-in-water emulsion cannot be maintained.

Patent Document 5 discloses a liquid composition for drinking containing coenzyme $Q_{10}$, a hydrophilic glycerol fatty acid ester and/or a hydrophilic sucrose fatty acid ester. The sucrose fatty acid ester used in this application is hydrophilic unlike the present invention, and the effect of preventing coenzyme $Q_{10}$ crystallization is not considered at all, which comes into question in the case where high ratio of coenzyme $Q_{10}$ is contained. Thus the stability of an oil-in-water emulsion is quite low.

Patent Document 6 discloses a technology of using polyglycerol with the average degree of polymerization of 10 together with a fatty acid monoester having 18 carbon atoms, and polyglycerol with the average degree of polymerization of 3 to 6 together with a fatty acid mono-, di-, tri-, or pentaester having 18 carbon atoms. The use of an unsaturated fatty acid such as oleic acid and linoleic acid is not suitable for long term preservation because of a worry of flavor deterioration due to oxidation deterioration and the like. Moreover, there may arise production difficulties in some cases, for example, high temperature is required in emulsification since a stearic acid ester itself has a high melting point.

Patent Document 7 discloses the effect of preventing coenzyme $Q_{10}$ crystallization provided by using sterol, a sterol derivative, and a derivative having a skeleton similar to that of sterol, and a stable emulsion. However, utilization of such sterols in general foods is actually hesitated in many cases, and also, an acid resistance and heat resistance are not taken into consideration at all in this application.

Patent Document 8 discloses a coenzyme $Q_{10}$-containing composition comprising a lipophilic polyhydric alcohol fatty acid ester and a hydrophilic polyhydric alcohol fatty acid ester, but there is no specific description regarding a lipophilic sucrose fatty acid ester, which is used in the present invention. Furthermore, stability of said composition is unclear so that no suggestion is given to the present invention by this application.

Patent Document 1: Japanese Kohyo Publication 2001-504343
Patent Document 2: Japanese Kokai Publication 2000-212066
Patent Document 3: Japanese Kokai Publication 2003-238396
Patent Document 4: Japanese Kokai Publication 2003-300870
Patent Document 5: Japanese Kokai Publication 2003-304847
Patent Document 6: Japanese Kokai Publication 2004-196781
Patent Document 7: Japanese Kokai Publication 2004-210669
Patent Document 8: International Publication WO04/064543

SUMMARY OF THE INVENTION

The present invention has for its object to provide a water soluble composition with high bioavailability, which causes no crystallization of coenzyme $Q_{10}$ during preservation, maintains a stable oil-in-water emulsion for a long period of time from refrigeration temperature to room temperature, and allows efficient supply.

The present inventors had made intensive investigations in view of the above-mentioned state of the art, and as a result, found that specific components have the effect of preventing coenzyme $Q_{10}$ crystallization, and by using these components, a water soluble composition which is stable for a long period of time can be obtained and finally, completed the present invention.

That is, the first aspect of the present invention is related to a coenzyme $Q_{10}$-containing water soluble composition which comprises coenzyme $Q_{10}$, a hydrophilic polyglycerol fatty acid ester, a lipophilic sucrose fatty acid ester, and an aqueous phase component.

A preferred embodiment is
the coenzyme $Q_{10}$-containing water soluble composition mentioned above,
wherein the hydrophilic polyglycerol fatty acid ester is a decaglycerol mono-saturated fatty acid ester constituted of a fatty acid residue containing 12 or more carbon atoms;
More preferred embodiment is
the coenzyme $Q_{10}$-containing water soluble composition mentioned above,
wherein the saturated fatty acid ester is at least one species selected from the group consisting of a laurate ester, a myristate ester and a palmitate ester;
Further preferred embodiment is
the coenzyme $Q_{10}$-containing water soluble composition mentioned above,
wherein the lipophilic sucrose fatty acid ester is an ester composed of higher fatty acid and acetic acid;
Further more preferred embodiment is
the coenzyme $Q_{10}$-containing water soluble composition mentioned above
which comprises 0.01 to 40% by weight of coenzyme $Q_{10}$ in the whole water soluble composition;
Particularly preferred embodiment is
the coenzyme $Q_{10}$-containing water soluble composition mentioned above,
wherein the content of the lipophilic polyglycerol fatty acid ester is 1 to 500 parts by weight to 100 parts by weight of coenzyme $Q_{10}$;
More particularly preferred embodiment is
the coenzyme $Q_{10}$-containing water soluble composition mentioned above,
wherein the content of the lipophilic sucrose fatty acid ester is 1 to 200 parts by weight to 100 parts by weight of coenzyme $Q_{10}$;
Further particularly preferred embodiment is
the coenzyme $Q_{10}$-containing water soluble composition mentioned above,
wherein the median size of emulsion particles in the water soluble composition is not larger than 100 nm;
And most preferred embodiment is
the coenzyme $Q_{10}$-containing water soluble composition mentioned above,
wherein the aqueous phase component is a polyhydric alcohol and/or water.

The second aspect of the present invention is related to a coenzyme $Q_{10}$-containing water-soluble dry powder which is obtained by drying the above-mentioned coenzyme $Q_{10}$-containing water soluble composition.

The third aspect of the present invention is related to a process for producing the above-mentioned coenzyme $Q_{10}$-containing water soluble composition which comprises making the median size of emulsion particles in the water soluble composition to be not larger than 100 nm by applying homogenization pressure of not less than 50 MPa.

The fourth aspect of the present invention is related to a food, functional food, beverage, pharmaceutical product, quasi drug, cosmetic, or animal food which is obtained by using the above-mentioned coenzyme $Q_{10}$-containing water soluble composition or the above-mentioned coenzyme $Q_{10}$-containing water-soluble dry powder.

DETAILED DESCRIPTION OF THE INVENTION

In the following, the present invention is described in detail.

The coenzyme $Q_{10}$-containing water-soluble composition of the present invention comprises coenzyme $Q_{10}$, a hydrophilic polyglycerol fatty acid ester, a lipophilic sucrose fatty acid ester and an aqueous phase component, and is an oil-in-water emulsion.

In the present invention, such an emulsion in which completely no water is contained as an aqueous phase component, e.g., one mainly composed of a polyhydric alcohol alone, is also referred to as an oil-in-water emulsion product provided that said aqueous phase component forms an emulsion form with an oil phase.

Coenzyme $Q_{10}$ to be used in the present invention is a compound represented by the following structure.

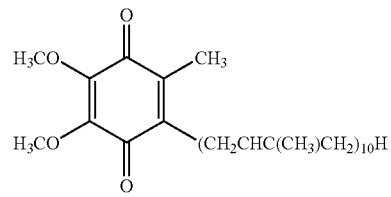

Coenzyme $Q_{10}$ used in the present invention is obtainable by conventionally known techniques such as a fermentation process, synthesis process, and extraction from animals and plants. But preferably used is, in view of application to the living body, one having an all-trans structure obtained by a fermentation process. For example, there may be mentioned Kaneka Coenzyme $Q_{10}$ (product of Kaneka Corporation).

In addition, the content of coenzyme $Q_{10}$ in the water soluble composition of the present invention is preferably 0.01 to 40% by weight, more preferably 1 to 30% by weight, and still more preferably 1 to 20% by weight in the whole water soluble composition. When the content of coenzyme $Q_{10}$ is less than 0.01% by weight, efficient supply of coenzyme $Q_{10}$ tends to become difficult, and when it exceeds 40% by weight, it tends to be difficult to obtain the water soluble composition stable for a long period of time.

The hydrophilic polyglycerol fatty acid ester to be used in the present invention preferably has its HLB value (hydrophile-lipophile balance) of not lower than 8, more preferably not lower than 10, and still more preferably not lower than 12. The HLB value can be obtained by the following formula (Chemical Dictionary (Kagaku Jiten), Tokyo Kagaku Dozin, the 1st edition, published on Oct. 1 (1994)).

$$HLB = 20 \times (1 - S/A)$$

S: saponification value of ester
A: acid value of fatty acid

The average degree of polymerization of glycerol is preferably not less than 6, and more preferably not less than 10.

The fatty acid constituting an ester preferably has not less than 12 carbon atoms and not more than 24 carbon atoms. Particularly, a saturated fatty acid is preferred, and more preferred is at least one species selected from the group consisting of a lauric acid, a myristic acid and a palmitic acid.

As the hydrophilic polyglycerol fatty acid ester, particularly preferred is a decaglycerol mono-saturated fatty acid ester constituted of a fatty acid residue containing 12 or more carbon atoms, and most preferred is a decaglycerol mono-palmitic acid ester.

The amount of addition of the above hydrophilic polyglycerol fatty acid ester is preferably 1 to 500 parts by weight, more preferably 10 to 500 parts by weight, still more preferably 30 to 500 parts by weight, particularly preferably 30 to 200 parts by weight, and most preferably 30 to 150 parts by weight to 100 parts by weight of coenzyme $Q_{10}$. When said amount of addition is less than 1 part by weight, it tends to be difficult to obtain a stable water soluble composition, and when it exceeds 500 parts by weight, although a water soluble composition can be obtained, the viscosity thereof tends to increase easily due to an excess addition of the polyglycerol fatty acid ester.

The lipophilic sucrose fatty acid ester to be used in the present invention is not particularly restricted as long as it has the effect of preventing coenzyme $Q_{10}$ crystallization in the dissolution state. As the fatty acid constituting an ester, one having 8 to 24 carbon atoms can be preferably mentioned, and particularly, one having 16 or more carbon atoms, i.e., so-called higher fatty acid is preferred. Said fatty acid constituting an ester may be any of a saturated fatty acid, unsaturated fatty acid or branched fatty acid, but a saturated fatty acid is particularly preferred.

As said lipophilic sucrose fatty acid ester, particularly preferred is an ester composed of higher fatty acid(s) and in which residual hydroxyl groups are acetylated as well, i.e., an ester composed of a higher fatty acid(s) and acetic acid(s).

As a specific example of the lipophilic sucrose fatty acid ester, there may be mentioned, for example, sucrose palmitate, sucrose stearate, an acetylation product thereof, and the like.

The amount of addition of the above lipophilic sucrose fatty acid ester is preferably 1 to 200 parts by weight, more preferably 5 to 150 parts by weight, still more preferably 10 to 100 parts by weight, and particularly preferably 30 to 100 parts by weight to 100 parts by weight of coenzyme $Q_{10}$. If the amount of addition is less than 1 part by weight, the effect of preventing crystallization tends to be insufficient, and if it exceeds 200 parts by weight, emulsification tends to be unstable even though the effect of preventing crystallization is exerted.

The aqueous phase component of the present invention contains a polyhydric alcohol and/or water.

The polyhydric alcohol is not particularly restricted as long as it is applicable for foods, and usable are glycerol, diglycerol, triglycerol, polyglycerol, propylene glycol, dipropylene glycol, 1,3-butylene glycol, ethylene glycol, polyethylene glycol, sucrose, fructose, glucose, lactose, trehalose, sorbitol, xilytol, maltitol, erythritol, mannitol, xylose, mannose, and the like. When a polyhydric alcohol is used as the aqueous phase component, at least one species of those mentioned above is used, and crystalline one can be used as an aqueous solution after addition of water. Among the above-mentioned polyhydric alcohols, preferred are glycerol and sorbitol.

Since the coenzyme $Q_{10}$-containing water soluble composition of the present invention is an oil-in-water emulsion, it is possible to add other oil soluble components and water soluble components.

In this case, the oil soluble component is not particularly restricted as long as it does not affect emulsification. Usable are, for example, vegetable oils such as corn oil, rapeseed oil, high erucic rapeseed oil, soybean oil, olive oil, safflower oil, cottonseed oil, sunflower oil, rice bran oil, Japanese basil oil, perilla oil, linseed oil, evening primrose oil, cacao butter, peanut oil, palm oil, and palm kernel oil; animal oils such as fish oil, beef tallow, lard, milk fat, and egg-yolk oil; synthetic oils such as medium chain fatty acid triglyceride; oils/fats derived from the above oils/fats by fractionation, hydrogenation, transesterification or the like, or mixed oils of such oils/fats; and the like. As other oil soluble components, there may be mentioned lipophilic vitamins such as vitamin A, D, E, K and P, lipophilic flavors, essential oils, colorants, antioxidants, specific gravity moderators, and the like.

The water soluble component is not particularly restricted within the range that emulsification is not affected, and there may be mentioned water soluble vitamins such as vitamin C, organic acids, various salts as tasting agents, and the like.

The process for producing the coenzyme $Q_{10}$-containing water soluble composition of the present invention is described below.

Predetermined amounts of coenzyme $Q_{10}$, the lipophilic sucrose fatty acid ester, and according to need, other optional component(s), i.e. the lipophilic component(s) are warmed to a predetermined temperature while stirring with a stirrer such as an ordinary turbine type or paddle type one, and dissolved to prepare an oil phase. In the same manner, the hydrophilic polyglycerol fatty acid ester and aqueous phase component(s) are warmed to a predetermined temperature, and dissolved to prepare an aqueous phase. In addition, the hydrophilic polyglycerol fatty acid ester may be added to the oil phase. The temperature at which each component is warmed to and dissolved to prepare the oil phase is not particularly restricted, but preferably 50 to 70° C. And the temperature at which each component is warmed to and dissolved to prepare the aqueous phase is not particularly restricted, but preferably 50 to 70° C.

Then, the oil phase is added to the prepared aqueous phase while stirring, and preliminary emulsification is carried out. For adjusting the particle diameter of the obtained pre-emulsion to a desired particle diameter according to need, emulsification is preferably carried out with a high-pressure homogenizer, and the like.

As an emulsification method for obtaining the coenzyme $Q_{10}$-containing water soluble composition of the present invention, there may be mentioned a mechanical emulsification method using a general homogenizer, and the like.

As an apparatus to be used for the mechanical emulsification method, there may be mentioned high speed stirring homogenizers such as T.K. Homomixer (manufactured by Tokushu Kika Kogyo Co., Ltd. (PRIMIX Corporation)), Fill Mix (manufactured by Tokushu Kika Kogyo Co., Ltd. (PRIMIX Corporation)), Poly-Tron (manufactured by KINEMATICA AG), Physcotron (manufactured by Microtec Nition Co., Ltd.), and Clearmix W Motion (manufactured by M Technique Co., Ltd.); high pressure homogenizers such as Microfluidizer (manufactured by Mizuho Industrial Co., Ltd.), Ultimizer System (manufactured by Sugino Machine Limited), Nanomizer (manufactured by Yoshida Kikai Co., Ltd.) and Manton-Gaulin type homogenizer; a colloid mill, an ultrasonic homogenizer, and the like.

Furthermore, other than the mechanical emulsification method, a membrane-emulsification method, microchannel emulsification method, natural emulsification method, phase inversion emulsification method, gel emulsification method, D-phase emulsification method, and the like can also be used.

By the above-mentioned emulsification method, the median size of emulsion particles in the coenzyme $Q_{10}$-containing water soluble composition of the present invention is adjusted to preferably not larger than 100 nm, more preferably 20 to 80 nm, still more preferably 30 to 80 nm, particularly preferably 35 to 80 nm, and most preferably 35 to 60 nm. If the median size exceeds 100 nm, the storage stability and transparency of the water soluble composition become insufficient and the effect of the present invention tends to be difficult to be obtained. Moreover, in view of the storage stability and transparency of the water soluble composition, smaller the median size of emulsion particles, more preferred. However, the median size of less than 20 nm is not practical since a large amount of emulsifier is required.

Herein, the median size of emulsion particles refers to a diameter of an oil portion in the oil-in-water emulsion of the coenzyme $Q_{10}$-containing water soluble composition (i.e., island part in the sea-island structure). The median size can be determined using a generally used particle size analyzer such as a laser diffraction particle size analyzer and a dynamic light scattering particle size analyzer.

For obtaining the desired median size (particularly the median size of not larger than 100 nm), it is preferable to use a high pressure homogenizer among the above-mentioned emulsification methods. When a high pressure homogenizer is used, the homogenization pressure is preferably adjusted to not lower than 20 MPa, more preferably not lower than 50 MPa, and still more preferably not lower than 100 MPa. When the homogenization pressure is lower than 20 MPa, the median size may not be not larger than 100 nm.

Moreover, since sharper distribution of the particle size gives better storage ability, it is preferable to carry out the high pressure emulsification process twice or more.

Furthermore, other emulsification method is applicable as long as the same level of shearing force as a high pressure homogenizer can be applied. For example, by using the above-mentioned Clearmix W Motion or Fill Mix and adjusting the stirring rate and stirring period properly, it is possible to make the median size not larger than 100 nm.

The temperature in the emulsification process is not particularly restricted as long as coenzyme $Q_{10}$, and the lipophilic sucrose fatty acid ester are dissolved, but preferably 50 to 80° C., and more preferably 60 to 80° C. When the process temperature exceeds 80° C., coenzyme $Q_{10}$ could be decomposed by heat.

Moreover, the coenzyme $Q_{10}$-containing water-soluble dry powder of the present invention can be obtained by drying the above-mentioned coenzyme $Q_{10}$-containing water soluble composition.

Furthermore, the coenzyme $Q_{10}$-containing water soluble composition and the coenzyme $Q_{10}$-containing water-soluble dry powder mentioned above can be used for a food, functional food, beverage, pharmaceutical product, quasi drug, cosmetic, animal food, and the like.

That is, the coenzyme $Q_{10}$-containing water soluble composition and the coenzyme $Q_{10}$-containing water-soluble dry powder of the present invention can be taken as they are or in a capsulated form, but they may also be utilized for beverages such as milk beverages, soft drinks, nutrition drinks, and drinks for beauty; confections such as chewing gum, chocolate, candies, jellies, biscuits and crackers; frozen sweets such as ice cream and ice candies; noodles such as Japanese wheat noodles, Chinese noodles, spaghetti, and instant noodles; fish paste foods such as fish minced and steamed (kamaboko), fish sausage (chikuwa), and minced flesh (hannpen); seasonings such as dressings, mayonnaise and sauces; bakery products, hams, soups, various retort foods, various frozen foods, and so forth. Furthermore, they also can be used for oral preparations (liquid medicines such as syrups, and solid preparations such as capsules, granulations, pills, powders and tablets), functional foods such as health drinks, and also can be used as pet foods or feeds for domestic animals. Furthermore, the coenzyme $Q_{10}$-containing water soluble composition and the coenzyme $Q_{10}$-containing water-soluble dry powder of the present invention can also be used, directly or after proper modification, for pharmaceutical products such as oral preparations (liquid medicines such as syrups, and solid preparations such as capsules, granulations, pills, powders and tablets), injections, nasal drops, eye drops, suppositories, sprays, ointments and patches; quasi drugs such as creams, suppositories, ointments, patches and toothpastes; cosmetics such as lotions, skin toner, creams and foundation, and the like.

Additionally, it is possible to obtain dry powders by adding an excipient such as dextrin or lactose and then removing water content by a spray-drying technique, etc. By dissolving the obtained dry powders in water, a coenzyme $Q_{10}$-containing aqueous solution can be prepared.

Effect of the Invention

According to the present invention, it is possible to produce a water soluble composition containing coenzyme $Q_{10}$, which has low solubility in water, and stable for a long period of time. Moreover, by using the water soluble composition of the present invention, it becomes possible to produce foods, drinks and the like with high bioavailability, which allows efficient supply, for example.

BEST MODE FOR CARRYING OUT THE INVENTION

The following examples illustrate the present invention in further detail. These examples are, however, by no means limitative of the scope of the invention.

Reference Examples 1 to 10

The component materials shown in Table 1 were warmed and dissolved at 60° C., and weighed out the appropriate amount on a measuring aluminum pan to make samples for DSC determination.

Explanations for each component shown in Table 1 are as follows (respective numbers are those described in Table 1).
1) Kaneka Coenzyme $Q_{10}$, product of Kaneka Corporation
2) DK-FA50, product of Dai-Ichi Kogyo Seiyaku Co., Ltd.
3) DK-FA10E, product of Dai-Ichi Kogyo Seiyaku Co., Ltd.
4) S-170, product of Mitsubishi-Kagaku Foods Corporation
5) Poem G508, product of Riken Vitamin Co., Ltd.
6) Emulsy MS, product of Riken Vitamin Co., Ltd.
7) Emulsy MO, product of Riken Vitamin Co., Ltd.
8) Actor M2, product of Riken Vitamin Co., Ltd.
9) PO-3S, product of Sakamoto Yakuhin Kogyo Co., Ltd.
10) Poem S-65F, product of Riken Vitamin Co., Ltd.

In addition, the fatty acid portions of the above 2) and 3) sucrose fatty acid esters are stearic acid and acetic acid (acetylated). The fatty acid portion of 4) sucrose fatty acid ester is stearic acid. The fatty acid portion of 5) acetic acid monoglyceride is stearic acid and acetic acid (acetylated). The fatty acid portion of 6) monoglyceride is stearic acid. The fatty acid portion of 7) monoglyceride is oleic acid. The fatty acid portion of 8) medium chain fatty acid triglyceride is caprylic acid. The fatty acid portion of 9) polyglycerol fatty acid ester is oleic acid. The fatty acid portion of 10) sorbitan fatty acid ester is stearic acid.

<Effect of Preventing Crystallization>

Using the samples obtained in Reference Examples 1 to 10, the effect of preventing coenzyme $Q_{10}$ crystallization derived from a lipophilic sucrose fatty acid ester was determined by DSC (differential scanning calorimetry).

DSC Determination
Detector: DSC6220 (manufactured by SII Nano Technology Inc.)
Determination condition: the crystallization peak (exothermic peak) of coenzyme $Q_{10}$ was determined after retaining the samples at 80° C. for 10 minutes and then cooling them to −50° C. at a cooling rate of −5° C./rain.

TABLE 1

| | (unit not mentioned: part by weight) Reference Example | | | | | | | | | |
|---|---|---|---|---|---|---|---|---|---|---|
| Component | 1 | 2 | 3 | 4 | 5 | 6 | 7 | 8 | 9 | 10 |
| Coenzyme $Q_{10}$ 1) | 10 | 10 | 10 | 10 | 10 | 10 | 10 | 10 | 10 | 10 |
| Sucrose fatty acid ester 2) | 5 | — | — | — | — | — | — | — | — | — |
| Sucrose fatty acid ester 3) | — | 5 | — | — | — | — | — | — | — | — |
| Sucrose fatty acid ester 4) | — | — | 5 | — | — | — | — | — | — | — |
| Acetic acid monoglyceride 5) | — | — | — | — | 5 | — | — | — | — | — |
| Monoglyceride 6) | — | — | — | — | — | 5 | — | — | — | — |
| Monoglyceride 7) | — | — | — | — | — | — | 5 | — | — | — |
| Medium chain fatty acid triglyceride 8) | — | — | — | — | — | — | — | 5 | — | — |
| Polyglycerol fatty acid ester 9) | — | — | — | — | — | — | — | — | 5 | — |
| Sorbitan fatty acid ester 10) | — | — | — | — | — | — | — | — | — | 5 |
| DSC exothermic peak (° C.) | Not detected | −46.5 | −14.9 | −11.4 | −5.6 | −10.4 | −3.3 | −18.4 | −12.7 | −9.6 |

Despite the sucrose fatty acid esters of Reference Examples 1 to 3 are solids, all these samples were found to prevent crystallization of coenzyme $Q_{10}$. In particular, DK-FA50 of Reference Example 1 (esterification ratio: stearic acid<acetic acid) and DK-FA10E of Reference Example 2 (esterification ratio: stearic acid>acetic acid), which are composed of stearic acid and acetic acid, are superior in the effect of preventing crystallization compared with S-170 of Reference Example 3 composed of stearic acid. And as for DK-FA50, a superior result was obtained that completely no crystallization occurred at the temperature higher than −50° C.

On the other hand, Poem G508 of Reference Example 5, which is also composed of stearic acid and acetic acid, promoted crystallization as in the case of the other monoglycerides (Reference Examples 6 and 7) and the sorbitan fatty acid ester (Reference Example 10). Moreover, medium chain fatty acid triglyceride (Reference Example 8) and PO-3S (Reference Example 9) in liquid form also promoted crystallization of coenzyme $Q_{10}$. From the fact that medium chain fatty acid triglyceride is considered to dissolve coenzyme $Q_{10}$ relatively well, this component supposedly serves as a solvent and makes super cooled condition to retard crystallization.

Example 1

According to the formulation and conditions shown in Table 2, a coenzyme $Q_{10}$-containing water soluble composition was prepared. Specifically, as an oil phase portion, 10 parts by weight of coenzyme $Q_{10}$ (Kaneka Coenzyme $Q_{10}$) and 5 parts by weight of a sucrose fatty acid ester (DK-FA50) were warmed to 70° C. and completely dissolved. In the same manner, as an aqueous phase portion, 10 parts by weight of decaglycerol monolaurate ester (L-7D) and 75 parts by weight of glycerol were warmed to 70° C. and completely dissolved. Then, the oil phase portion was added to the aqueous phase portion while stirring, and the obtained mixture was processed, using Nanomizer II (manufactured by Yoshida Kikai Co., Ltd.), 5 times at the emulsification pressure of 100 MPa to obtain a coenzyme $Q_{10}$-containing water soluble composition.

Example 2 to 18 and Comparative Examples 1 to 3

According to the formulations and conditions shown in Table 2, coenzyme $Q_{10}$-containing water soluble compositions were obtained in the same manner as Example 1.

Explanations for each component shown in Table 2 are as follows (respective numbers are those described in Table 2).
1) Kaneka Coenzyme $Q_{10}$, product of Kaneka Corporation
2) L-7D, product of Mitsubishi-Kagaku Foods Corporation
3) M-7D, product of Mitsubishi-Kagaku Foods Corporation
4) P-8D, product of Mitsubishi-Kagaku Foods Corporation
5) MO-7S, product of Sakamoto Yakuhin Kogyo Co., Ltd.
6) Q18S, product of Taiyou Kagaku Co., Ltd.
7) DK-FA50, product of Dai-Ichi Kogyo Seiyaku Co., Ltd.
8) DK-FA10E, product of Dai-Ichi Kogyo Seiyaku Co., Ltd.
9) S-170, product of Mitsubishi-Kagaku Foods Corporation
10) Poem G508, product of Riken Vitamin Co., Ltd.
11) Actor M2, product of Riken Vitamin Co., Ltd.
12) Poem S-65F, product of Riken Vitamin Co., Ltd.
13) Product of Sakamoto Yakuhin Kogyo Co., Ltd.

In addition, the fatty acid portions of the above 7) and 8) sucrose fatty acid esters are stearic acid and acetic acid (acetylated). The fatty acid portion of 9) sucrose fatty acid ester is stearic acid. The fatty acid portion of 10) acetic acid monoglyceride is stearic acid and acetic acid (acetylated). The fatty acid portion of 11) medium chain fatty acid triglyceride is caprylic acid. The fatty acid portion of 12) sorbitan fatty acid ester is stearic acid.

Using the coenzyme $Q_{10}$-containing water soluble compositions obtained in Examples and Comparative Examples mentioned above, the particle diameter and stability was determined and evaluated as follows. The results are shown in Table 2.

<Median Size of Emulsion Particles in the Water Soluble composition>

The median size of emulsion particles in the water soluble compositions obtained in Examples 1 to 18 and Comparative Examples 1 to 3 was determined by using LB-550 (manufactured by Horiba, Ltd.; a dynamic light scattering particle size analyzer) according to its manual, and putting the water soluble compositions into a measuring cell.

<Stability Evaluation of the Water Soluble Composition>

The water soluble compositions obtained in Examples 1 to 18 and Comparative Examples 1 to 3 were stored in incubators each set at 4° C., 25° C. or 40° C., and conditions of the compositions were observed with eyes for evaluation. The evaluation criteria are as follows. Excellent: Stable and no change observed for not less than 6 months, Fair: stable and no change observed for 3 months, Good: stable and no change observed for 1 month, and Bad: change of state such as aggregation, separation and solidification occurred within 1 month.

TABLE 2

| | | Example | | | | | | | | | |
|---|---|---|---|---|---|---|---|---|---|---|---|
| | | 1 | 2 | 3 | 4 | 5 | 6 | 7 | 8 | 9 | 10 |
| Formulation | Coenzyme $Q_{10}$ 1) | 10 | 10 | 10 | 10 | 10 | 1 | 5 | 10 | 10 | 15 |
| | Decaglycerol monolaurate ester 2) | 10 | — | — | — | — | — | — | — | — | — |
| | Decaglycerol monomyristate ester 3) | — | 10 | — | — | — | — | — | — | — | — |
| | Decaglycerol monopalmitate ester 4) | — | — | 10 | 10 | 10 | 5 | 10 | 10 | 15 | 10 |
| | Decaglycerol monooleate ester 5) | — | — | — | — | — | — | — | — | — | — |
| | Decaglycerol monostearate ester 6) | — | — | — | — | — | — | — | — | — | — |
| | Sucrose fatty acid ester 7) | 5 | 5 | 3 | 5 | 5 | 1 | 3 | 5 | 5 | 5 |
| | Sucrose fatty acid ester 8) | — | — | — | — | — | — | — | — | — | — |
| | Sucrose fatty acid ester 9) | — | — | — | — | — | — | — | — | — | — |
| | Acetic acid monoglyceride 10) | — | — | — | — | — | — | — | — | — | — |
| | Medium chain fatty acid triglyceride 11) | — | — | — | — | — | — | — | — | — | — |
| | Sorbitan fatty acid ester 12) | — | — | — | — | — | — | — | — | — | — |
| | Glycerol 13) | 75 | 75 | 77 | 75 | 75 | 93 | 82 | 75 | 60 | 70 |
| | Water | — | — | — | — | — | — | — | — | 10 | — |
| Emulsification | Emulsification pressure (MPa) | 100 | 100 | 100 | 20 | 50 | 100 | 100 | 100 | 200 | 100 |
| | Median size (nm) | 49 | 49 | 45 | 79 | 55 | 38 | 42 | 47 | 45 | 60 |
| STability | Stored at 4° C. | Excellent | Excellent | Fair | Fair | Excellent | Excellent | Excellent | Excellent | Excellent | Excellent |
| | Stored at 25° C. | Fair | Excellent | Fair | Good | Excellent | Excellent | Excellent | Excellent | Excellent | Excellent |
| | Stored at 40° C. | Good | Fair | Fair | Good | Excellent | Excellent | Excellent | Excellent | Excellent | Excellent |

| | | Example | | | | | | | | Compar. Ex. | | |
|---|---|---|---|---|---|---|---|---|---|---|---|---|
| | | 11 | 12 | 13 | 14 | 15 | 16 | 17 | 18 | 1 | 2 | 3 |
| Formulation | Coenzyme $Q_{10}$ 1) | 30 | 10 | 10 | 10 | 10 | 10 | 10 | 10 | 10 | 10 | 10 |
| | Decaglycerol monolaurate ester 2) | — | — | — | — | — | — | — | — | — | — | — |
| | Decaglycerol monomyristate ester 3) | — | — | — | — | — | — | — | — | — | — | — |
| | Decaglycerol monopalmitate ester 4) | 10 | 10 | 10 | 10 | — | — | 10 | 10 | 10 | 10 | 10 |
| | Decaglycerol monooleate ester 5) | — | — | — | — | 10 | — | — | — | — | — | — |
| | Decaglycerol monostearate ester 6) | — | — | — | — | — | 10 | — | — | — | — | — |
| | Sucrose fatty acid ester 7) | 10 | 5 | 5 | 5 | 5 | 5 | — | — | — | — | — |
| | Sucrose fatty acid ester 8) | — | — | — | — | — | — | 5 | — | — | — | — |
| | Sucrose fatty acid ester 9) | — | — | — | — | — | — | — | 5 | — | — | — |
| | Acetic acid monoglyceride 10) | — | — | — | — | — | — | — | — | 5 | — | — |
| | Medium chain fatty acid triglyceride 11) | — | — | — | — | — | — | — | — | — | 5 | — |
| | Sorbitan fatty acid ester 12) | — | — | — | — | — | — | — | — | — | — | 5 |
| | Glycerol 13) | 50 | 65 | 55 | 25 | 75 | 75 | 75 | 75 | 75 | 75 | 75 |
| | Water | — | 10 | 20 | 50 | — | — | — | — | — | — | — |
| Emulsification | Emulsification pressure (MPa) | 100 | 100 | 100 | 100 | 100 | 100 | 100 | 100 | 100 | 100 | 100 |
| | Median size (nm) | 66 | 53 | 57 | 73 | 56 | 55 | 49 | 44 | 59 | 49 | 53 |
| STability | Stored at 4° C. | Fair | Excellent | Excellent | Excellent | Fair | Fair | Excellent | Fair | Fair | Fair | Fair |
| | Stored at 25° C. | Fair | Excellent | Excellent | Fair | Good | Fair | Fair | Good | Bad | Bad | Bad |
| | Stored at 40° C. | Fair | Excellent | Fair | Fair | Good | Fair | Good | Good | Bad | Bad | Bad |

From the above results, it was found that the compositions of Examples 1 to 18 according to the present invention showed superior stability at any temperatures of 4° C., 25° C. or 40° C., on the other hand the compositions of Comparative Examples 1 to 3 in which other fatty acid ester was used in lieu of a sucrose fatty acid ester were remarkably low in stability at 25° C. and 40° C.

Example 19 and Comparative Examples 4 to 5

Bioabsorbability Test

The coenzyme $Q_{10}$-containing water soluble composition obtained in Example 8 or coenzyme $Q_{10}$ was fed to a rat, and the concentration of coenzyme $Q_{10}$ in plasma was determined to evaluate the bioabsorbability of coenzyme $Q_{10}$ under the following conditions.
<Animals to be Used>
In the test, Slc: 7-week-old SD male rats (Japan SLC, Inc.) were used. After one week of preparatory breeding, they were used in testing when they turned 8-week-old. The rats were bred in a breeding room adjusted at temperature of 20 to 26° C., humidity of 40 to 70%, and lightening with 12 hours/day, while they were allowed to free access to a solid feed CE-2 (Clea Japan, Inc.) and tap water.
<Samples and Supplying Form>
The rats were fed with the test samples in the supplying forms, as shown in Table 3. In Example 19, distilled water was added to the coenzyme $Q_{10}$-containing water soluble composition of Example 8, and an adjustment was carried out in order to make the supplying amount (i.e., the supplying amount of coenzyme $Q_{10}$ itself, hereinafter the same shall apply) and the supplying volume (the supplying volume of the whole solution comprising the coenzyme $Q_{10}$-containing water soluble composition and distilled water) to be 30 mg/kg and 3 ml/kg, respectively. In Comparative Example 4, coenzyme $Q_{10}$ was dissolved by heating and mixed with soybean oil, and an adjustment was carried out in order to make the supplying amount and supplying volume (the supplying volume of the whole solution comprising coenzyme $Q_{10}$ and soybean oil) to be 30 mg/kg and 3 ml/kg, respectively. In Comparative Example 5, coenzyme $Q_{10}$ was added to a 0.5 (W/V) % CMC-Na aqueous solution, and an adjustment was carried out in order to make the supplying amount and supplying volume (the supplying volume of the whole suspension comprising coenzyme $Q_{10}$ and the CMC-Na aqueous solution) to be 30 mg/kg and 10 ml/kg, respectively. The obtained solution was applied with ultrasonic wave to produce a suspension.

TABLE 3

| | Test sample | Supplying form |
| --- | --- | --- |
| Example 19 | Coenzyme $Q_{10}$-containing water soluble composition of Example 8 | Solution in distilled water |
| Compar. Ex. 4 | Coenzyme $Q_{10}$ powder | Solution in soy bean oil |
| Compar. Ex. 5 | Coenzyme $Q_{10}$ powder | Suspension in a 0.5(W/V)% CMC-Na aqueous solution |

<Bioabsorbability Test>
As a supplying route, a stomach tube was used and oral supplying was carried out forcedly.
As a process for blood sampling, 0.5 ml of blood was sampled from the jugular vein using a heparin-added syringe 1, 2, 4, 8 and 24 hours later from supplying. After that, plasma was immediately separated with a cooling centrifugal machine (4° C., 3,000 rpm×20 min.), and the obtained plasma was stored in a freezer at −20° C. until analysis.
As a process for determination, coenzyme $Q_{10}$ in plasma was extracted with a conventional method, and determined with a high performance liquid chromatography (HPLC). That is, a 1% $FeCl_3$ aqueous solution (0.01 ml), ion-exchanged water (0.5 ml), and methanol (2.0 ml) were added to plasma (0.2 ml). To this mixed solution, hexane (3.0 ml) was added and shaken to extract coenzyme $Q_{10}$. Then, hexane was separated, and the residue was evaporated to dryness and dissolved in ethanol (0.2 ml) to be determined. The HPLC conditions at that time were as follows.
HPLC Conditions
Detector: an ultraviolet absorption photometer
Detection wavelength: 275 nm
Column: YMC-Pack ODS-A303 (manufactured by YMC Co., Ltd.)
Mobile phase: methanol/hexane=88/12 (volume ratio)
Flow rate: 1 ml/min
Analysis time: 40 min.
<Results>
Table 4 and FIG. 1 show the determination results of the concentration of coenzyme $Q_{10}$ in plasma. In Example 19, the highest concentration (Cmax) in plasma was as high as 2.4 times and the concentration integration value in plasma ($AUC_{1-24}$) was as high as 2.5 times as compared with Comparative Example 4. Similarly, the values of Cmax and $AUC_{1-24}$ were both as high as 1.8 times as compared with Comparative Example 5. As observed above, the coenzyme $Q_{10}$-containing water soluble composition of the present invention showed quite excellent bioabsorbability (bioabsorbability of coenzyme $Q_{10}$).

TABLE 4

(Values in table: average ± standard deviation(SD))

| | Concentration of coenzyme $Q_{10}$ in plasma (μg/ml) | | | | | |
| --- | --- | --- | --- | --- | --- | --- |
| | 1 | 2 | 4 | 8 | 24 (hr) | $AUC_{1-24}$ |
| Example 19 | 0.99 ± 0.35 | 0.80 ± 0.48 | 0.99 ± 0.53 | 1.80 ± 0.64 | 0.29 ± 0.08 | 24.98 ± 8.04 |
| Compar. Ex. 4 | 0.40 ± 0.09 | 0.75 ± 0.23 | 0.70 ± 0.49 | 0.39 ± 0.15 | 0.32 ± 0.09 | 10.08 ± 2.32 |
| Compar. Ex. 5 | 0.47 ± 0.17 | 0.99 ± 0.40 | 0.74 ± 0.19 | 0.76 ± 0.26 | 0.27 ± 0.08 | 13.96 ± 2.85 | n = 4

Example 20

A coenzyme $Q_{10}$-containing beverage: a coenzyme $Q_{10}$-containing beverage comprising 0.3 g of the coenzyme $Q_{10}$ containing water soluble composition of Example 5, 10.7 g of fructose glucose liquid sugar, 0.18 g of citric acid, 0.04 g of trisodium citrate and 88.78 g of water was prepared and sterilized at 85° C. for 30 minutes. No aggregation, separation, solidification, or the like was found and the obtained coenzyme $Q_{10}$-containing beverage remained transparent. As observed above, the coenzyme $Q_{10}$-containing water soluble composition of the present invention is quite stable even after being heated under acidic condition.

INDUSTRIAL APPLICABILITY

According to the present invention, it is possible to produce a water soluble composition containing coenzyme $Q_{10}$, which has very low solubility in water, and stable for a long period of time. Moreover, by using the water soluble composition of the present invention, it becomes possible to produce foods, drinks and the like with high bioavailability, which allows efficient supply, for example.

BRIEF DESCRIPTION OF THE DRAWING

FIG. 1 is a graph showing the result of the absorption test in rat (n=4, Mean±SD).

The invention claimed is:

1. A coenzyme $Q_{10}$-containing water soluble composition which comprises coenzyme $Q_{10}$, a hydrophilic polyglycerol fatty acid ester, a lipophilic sucrose fatty acid ester, and an aqueous phase component,
wherein the hydrophilic polyglycerol fatty acid ester is a decaglycerol mon-saturated fatty acid ester constituted of a fatty acid residue containing 12 or more carbon atoms.

2. The coenzyme $Q_{10}$-containing water soluble composition according to claim 1, wherein the saturated fatty acid ester is at least one species selected from the group consisting of a laurate ester, a myristate ester and a palmitate ester.

3. The coenzyme $Q_{10}$-containing water soluble composition according to claim 1, wherein the lipophilic sucrose fatty acid ester is an ester composed of a higher fatty acid and acetic acid.

4. The coenzyme $Q_{10}$-containing water soluble composition according to claim 1, which comprises 0.01 to 40% by weight of coenzyme $Q_{10}$ in the whole water soluble composition.

5. The coenzyme $Q_{10}$-containing water soluble composition according to claim 1, wherein the content of the hydrophilic polyglycerol fatty acid ester is 1-10 to 500 parts by weight to 100 parts by weight of coenzyme $Q_{10}$.

6. The coenzyme $Q_{10}$-containing water soluble composition according to claim 1, wherein the content of the lipophilic sucrose fatty acid ester is 1 to 200 parts by weight to 100 parts by weight of coenzyme $Q_{10}$.

7. The coenzyme $Q_{10}$-containing water soluble composition according to claim 1, wherein the aqueous phase component is a polyhydric alcohol and/or water.

8. A coenzyme $Q_{10}$-containing water-soluble dry powder which is obtained by drying the coenzyme $Q_{10}$-containing water soluble composition according to claim 1.

9. A food, functional food, beverage, pharmaceutical product, quasi drug, cosmetic, or animal food which is obtained by using the coenzyme $Q_{10}$-containing water soluble composition according to claim 1 or which is obtained by using a coenzyme $Q_{10}$-containing water-soluble dry powder which is obtained by drying the coenzyme $Q_{10}$-containing water soluble composition according to claim 1.

10. The coenzyme $Q_{10}$-containing water soluble composition according to claim 1 which is an oil-in-water emulsion.

11. The coenzyme $Q_{10}$-containing water soluble composition according to claim 10, wherein the median size of emulsion particles in the water soluble composition is not larger than 100 nm.

12. The coenzyme $Q_{10}$-containing water soluble composition according to claim 1, wherein the aqueous phase component is a mixture of a polyhydric alcohol and water, and the polyhydric alcohol is selected from the group consisting of glycerol and sorbitol.

* * * * *